(12) United States Patent
Doane et al.

(10) Patent No.: US 7,423,090 B2
(45) Date of Patent: *Sep. 9, 2008

(54) METHODS OF MAKING AND USING A SUPERABSORBENT POLYMER PRODUCT INCLUDING A BIOACTIVE, GROWTH-PROMOTING ADDITIVE

(75) Inventors: William McKee Doane, Morton, IL (US); Steven William Doane, Lebanon, OR (US); Milan H. Savich, Beaverton, OR (US)

(73) Assignee: Absorbent Technologies, Inc., Beaverton, OR (US)

( * ) Notice: Subject to any disclaimer, the term of this patent is extended or adjusted under 35 U.S.C. 154(b) by 337 days.

This patent is subject to a terminal disclaimer.

(21) Appl. No.: 11/013,664

(22) Filed: Dec. 15, 2004

(65) Prior Publication Data

US 2005/0159315 A1 Jul. 21, 2005

Related U.S. Application Data

(60) Provisional application No. 60/529,949, filed on Dec. 15, 2003.

(51) Int. Cl.
C08H 5/04 (2006.01)
C08B 37/00 (2006.01)
C09D 103/04 (2006.01)

(52) U.S. Cl. .................. 525/242; 525/54.3; 525/330.1; 525/360; 527/103; 527/312; 428/327; 428/402; 428/403

(58) Field of Classification Search .................. None
See application file for complete search history.

(56) References Cited

U.S. PATENT DOCUMENTS

| | | | |
|---|---|---|---|
| 3,244,500 A | 4/1966 | Stinson | 71/1 |
| 3,935,099 A | 1/1976 | Weaver et al. | 210/43 |
| 3,981,100 A | 9/1976 | Weaver et al. | 47/58 |
| 3,985,616 A | 10/1976 | Weaver et al. | 195/63 |
| 3,997,484 A | 12/1976 | Weaver et al. | 260/17.4 GC |
| 4,076,663 A | 2/1978 | Masuda et al. | 260/17.4 GC |
| 4,093,542 A | 6/1978 | Dahmen et al. | 210/54 |
| 4,113,685 A | 9/1978 | Hübner et al. | 260/29.4 |
| 4,134,863 A | 1/1979 | Fanta et al. | 260/17.4 GC |
| 4,155,888 A | 5/1979 | Mooth | 524/314 |
| 4,194,998 A | 3/1980 | Fanta et al. | 260/17.4 GC |
| 4,323,487 A | 4/1982 | Jones et al. | 525/54.32 |
| 4,367,297 A | 1/1983 | Hübner et al. | 523/130 |
| 4,408,073 A | 10/1983 | Goosens et al. | 564/204 |
| 4,459,068 A | 7/1984 | Erickson | 405/264 |
| 4,483,950 A | 11/1984 | Fanta et al. | 524/48 |
| 4,528,350 A | 7/1985 | Goosens et al. | 526/307 |
| 4,711,919 A | 12/1987 | Peppmöller et al. | 524/77 |
| 4,766,173 A | 8/1988 | Bailey et al. | 524/819 |
| 4,773,967 A | 9/1988 | Peppmöller et al. | 162/168.2 |
| 4,983,390 A | 1/1991 | Levy | 424/404 |
| 5,118,719 A | 6/1992 | Lind | 521/92 |
| 5,122,544 A | 6/1992 | Bailey et al. | 521/40.5 |
| 5,147,343 A | 9/1992 | Kellenberger | 604/368 |
| 5,154,713 A | 10/1992 | Lind | 604/358 |
| 5,176,797 A | 1/1993 | Hartan et al. | 162/168.3 |
| 5,221,313 A | 6/1993 | Mortvedt et al. | 71/63 |
| 5,292,404 A | 3/1994 | Hartan et al. | 162/164.6 |
| 5,350,799 A * | 9/1994 | Woodrum et al. | 525/54.3 |
| 5,512,646 A | 4/1996 | Hartan et al. | 526/292.95 |
| 5,567,478 A | 10/1996 | Houben et al. | 427/342 |
| 5,821,286 A | 10/1998 | Xu et al. | 524/47 |
| 5,853,848 A | 12/1998 | Fisk | 428/143 |
| 5,856,370 A | 1/1999 | Chmelir | 521/128 |
| 5,965,149 A * | 10/1999 | Silver | 424/405 |
| 6,048,467 A | 4/2000 | Dahmen et al. | 252/8.57 |
| 6,221,832 B1 | 4/2001 | Casteel et al. | 510/446 |
| 6,228,964 B1 | 5/2001 | Hartan et al. | 526/307 |
| 6,232,285 B1 | 5/2001 | Casteel et al. | 510/446 |
| 6,303,560 B1 | 10/2001 | Hartan et al. | 510/446 |
| 6,660,819 B2 | 12/2003 | Chmelir et al. | 526/217 |
| 6,758,152 B2 | 7/2004 | Steadman | 111/128 |
| 6,800,712 B2 | 10/2004 | Doane et al. | 527/312 |
| 6,889,471 B2 | 5/2005 | Arnold et al. | 47/58.1 SC |
| 7,009,020 B2 * | 3/2006 | Doane et al. | 527/103 |
| 2003/0020043 A1* | 1/2003 | Barresi et al. | 252/194 |
| 2004/0074271 A1 | 4/2004 | Krysiak et al. | 71/27 |
| 2006/0047068 A1* | 3/2006 | Doane et al. | 525/54.3 |
| 2006/0058502 A1* | 3/2006 | Doane et al. | 530/200 |
| 2007/0015878 A1* | 1/2007 | Savich et al. | 525/242 |
| 2007/0044528 A1 | 3/2007 | Kitchen | 71/28 |

OTHER PUBLICATIONS

Burkhardt et al. Plastic,Processing, Ullmann's Encyclopedia of Industrial Chemistry, Abstrct and pp. 1-5, Jun. 15, 2000.*
Stockosorb Agro; David W. Cox, 2004 Scholarship Report available at: http://nuffield.com.au/report_f/2004/David%20Cox%202004%20report.pdf (Aug. 19, 2006).
Press release titled, "A New Way of Reducing Water Consumption". (Nov. 7, 2001) http://ewire.com/displayccfm/Wire_ID/809.

(Continued)

*Primary Examiner*—Vasu Jagannathan
*Assistant Examiner*—Gennadiy Mesh
(74) *Attorney, Agent, or Firm*—Stoel Rives LLP

(57) ABSTRACT

A method of and a product formed by entrapping a bioactive, growth-promoting additive in a starch matrix to form a starch-based, superabsorbent polymer product for use in agricultural applications involves (1) graft polymerizing a monomer and a starch to form a starch graft copolymer including a starch matrix; (2) isolating the starch graft copolymer; (3) forming particles of starch graft copolymer; and (4) adding a bioactive, growth-promoting additive such that at least some of the bioactive, growth-promoting additive is entrapped by the starch matrix. Following placement of the starch-based SAP including a bioactive, growth-promoting additive in proximity to a plant, root, seed, or seedling, growth of the plant, root, seed, or seedling is promoted because availability of beneficial nutrients is increased.

34 Claims, No Drawings

OTHER PUBLICATIONS

Mikkelsen, Robert L.; "Using Hydrophilic Polymers to Control Nutrient Release" Fertilizer Research 38: 53-59, 1994.

Mikkelsen, Robert L. et al.; "Addition of Gel-Forming Hydrophilic Polymers to Nitrogen Fertilizer Solutions". Fertilizer Solutions, Fertilizer Research 36: 55-61, 1993.

Thompson, C. A.; "Effects of Stockosorb on Grain Sorghum in Central Kansas". 1998 Kansas Fertilizer Research Report of Progress 829; p. 36-46; Kansas State University-Manhattan, Kansas.

Thompson, C. A.; "Effects of the Cross-Linked Polyacrylamide Stockosorb on Wheat, Triticale, and Grain and Forage Sorghums in Central Kansas". 1999 Kansas Fertilizer Research Report of Progress 847; p. 21-35; Kansas State University-Manhattan, Kansas.

Thompson, C. A.; "Effects of the Cross-Linked Polyacrylamide Stockosorb on Winter Wheat, Triticale, and Grain and forage Sorghum in Central Kansas". 2000 Kansas Fertilizer Research Report of Progress 868; p. 29-40; Kansas State University-Manhattan, Kansas.

Office Action mailed on Mar. 19, 2007 in regard to Patent Application No. 11/500,698.

Office Action mailed on Aug. 2, 2007 in regard to Patent Application No. 11/500,698.

Office Action mailed on Jan. 16, 2007 in regard to Patent Application No. 11/269,214.

Office Action mailed on Sep. 17, 2007 in regard to Patent Application No. 11/269,214.

Office Action mailed on Oct. 22, 2007 in regard to Patent Application No. 11/213,563.

Office Action mailed on May 9, 2007 in regard to Patent Application No. 11/213,563.

"Starch-Encapsulated Pesticides: ARS Papers Presented at the International Seminar on Research and Development of Controlled-Release Formulations of Pesticides". Vienna, Austria Sep. 6-10, 1993 United States Department of Agriculture; Agricultural Service; 1995-1; Nov. 1994.

* cited by examiner

METHODS OF MAKING AND USING A SUPERABSORBENT POLYMER PRODUCT INCLUDING A BIOACTIVE, GROWTH-PROMOTING ADDITIVE

RELATED APPLICATION

This application claims the benefit under 35 U.S.C. §119(e) of U.S. Provisional Patent Application No. 60/529,949, filed Dec. 15, 2003.

The claimed invention was made as a result of activities undertaken within the scope of a joint research agreement between Milan H. Savich, Steven Doane and William Doane.

TECHNICAL FIELD

The present invention relates to agricultural amendments, and more particularly to methods of making and using a superabsorbent polymer product including a bioactive, growth-promoting additive.

BACKGROUND INFORMATION

Over the past three decades, polymer chemists and soil scientists have developed controlled-release pesticides for agricultural use. The two primary goals of controlled-release pesticides are (1) to increase efficacy of the pesticide and (2) to reduce negative environmental consequences of pesticide application. Some prior art controlled-release pesticides have been encapsulated in starch. These prior art starch-encapsulated controlled-release pesticide products are typically formed by mixing starch and pesticides and forming balls of the mixture. These starch-encapsulated pesticides provide rate-limited release of the pesticide particles from the starch, which release is governed largely by diffusion. Specifically, when starch-encapsulated pesticides are applied to the soil, they imbibe water and swell such that the pesticide particles diffuse out of the starch matrix into the soil surrounding a plant, root, seed, or seedling.

In 1976, polymer chemists developed a class of materials referred to as superabsorbent polymers (SAPs) (see, e.g., U.S. Pat. Nos. 3,935,099; 3,981,100; 3,985,616; and 3,997,484, all issued in 1976). SAPs are materials that imbibe or absorb at least 10 times their own weight in aqueous fluid and that retain the imbibed or absorbed aqueous fluid under moderate pressure. The imbibed or absorbed aqueous fluid is taken into the molecular structure of the SAP rather then being contained in pores from which the fluid could be eliminated by squeezing. Some SAPs can absorb up to 1,000 times their weight in aqueous fluid.

One type of SAPs, called "totally synthetic copolymers," is made by copolymerizing acrylic acid and acrylamide in the presence of a coupling agent. Almost all totally synthetic copolymer SAPs are used in baby diapers, adult diapers, catamenials, hospital bed pads, cable coating, and the like. Today the worldwide market for totally synthetic copolymer SAPs is estimated to be about 2 billion pounds per year.

Another type of SAPs, called starch graft copolymers, use a natural polymer, such as a starch, to form an SAP product including a starch graft copolymer. Films of starch graft copolymer SAP are typically formed by drying the starch graft copolymer composition on a tray or heating the composition on a drum dryer. The resulting films can then be ground or milled into flakes or powders. Films of starch graft copolymer SAP may also be made by diluting a viscous mixture of alkali starch graft copolymer with a water-miscible organic solvent such as alcohol or acetone to precipitate an alkali starch graft copolymer. The precipitated alkali starch graft copolymer is then isolated in a fine, powdery form by filtration and additional drying. Starch graft copolymer SAP products that absorb large quantities of aqueous fluids are typically marketed as absorbent soft goods that increase the water-holding capacity of soil and that form a coating on fibers, clay, paper, and the like.

The aqueous fluid absorption capabilities of SAPs have long made them desirable to agricultural companies. However, testing of the totally synthetic copolymer SAPs and the film or powdery starch graft copolymer SAPs showed poor agricultural performance, largely due to the particle size of the SAP products (small, fine particles measuring about 80 mesh in size). One inherent limitation of finer-mesh particles is that they cannot be used in typical granule applicators, which require particle sizes of at least 25 mesh. Further, the fine powders and/or films are often carried away by any wind present during application of the SAP product onto a field or a growing substrate.

While pesticide particles mixed with starch have been manufactured for many years, no one has successfully entrapped pesticides in a starch-based SAP product appropriate for use in large-scale agricultural applications. The inventors of the present invention recognized a need in the agricultural industry for a method of forming a starch-based SAP product including a bioactive, growth-promoting additive whose application to plants, roots, seedling, or seeds, or to a growing substrate in proximity to plants, roots, seedling, or seeds, promotes growth of the plants, roots, seedling, or seeds.

SUMMARY

One object of the present invention is to formulate a method of producing and using in agricultural applications a starch-based SAP product that includes a bioactive, growth-promoting additive. Application of the resulting SAP product promotes growth of a plant, root, seedling, or seed placed in proximity to the SAP product.

Preferred embodiments of the present invention generally relate to methods of and products formed by entrapping particles of bioactive, growth-promoting additive in a starch matrix to form a starch-based SAP product including a bioactive, growth-promoting additive for use in large-scale agricultural applications. Following application of the starch-based SAP product to a plant, root, seed, or seedling, or to a growing substrate in proximity to a plant, root, seed, or seedling, the starch-based SAP product promotes the availability of beneficial nutrients to the plant, root, seed, or seedling. Increasing the availability of these nutrients effects an increase in crop yield, growth rate, seed germination, and/or plant size. The bioactive, growth-promoting additive is physically held by and taken into the starch matrix portion of the SAP product, thereby forming a stable SAP product and minimizing or eliminating runoff of the additive during heavy rainfall, squeezing, or jarring during transport. It is believed that plants, roots, and seedlings withdraw the active portion of the bioactive, growth-promoting additive from the starch-based SAP product through capillary action, and that seeds utilize the bioactive, growth-promoting additive by diffusion of the additive from the starch matrix.

A preferred method of forming an SAP product including a bioactive, growth-promoting additive involves (1) graft polymerizing at least one grafting reagent and a starch to form a starch graft copolymer including a starch matrix; (2) isolating the resulting starch graft copolymer; (3) forming films, powders, or particles of starch graft copolymer that are sized for use in agricultural applications; and (4) adding the bioactive, growth-promoting additive so that at least some of the bioactive, growth-promoting additive is entrapped by the starch matrix. Addition of the bioactive, growth-promoting additive may occur at various times during this process, depending on the type of additive and the desired degree of entrapment of the additive within the starch matrix.

There are at least two preferred implementations of this preferred method of forming the starch-based SAP product including a bioactive, growth-promoting additive. A first preferred implementation involves (1) combining a monomer and a starch in the presence of an initiator such that the monomer graft polymerizes onto the starch to form a mixture including a starch graft copolymer having a starch matrix; (2) saponifying the mixture; (3) precipitating the saponified starch graft copolymer from the mixture to form particles of SAP product that are sized for use in agricultural applications; and (4) adding the bioactive, growth-promoting additive so that at least some of the bioactive, growth-promoting additive is entrapped by the starch matrix. Addition of the bioactive, growth-promoting additive may occur, for example, during at least one of the following processing steps: (1) while combining the monomer and the starch; (2) following saponification of the starch graft copolymer; and (3) following formation of the starch-based SAP product.

A second preferred implementation of the preferred method involves (1) graft polymerizing a monomer onto a starch in the presence of an initiator to form a mixture including a starch graft copolymer having a starch matrix; (2) adding a cross-linking agent to the mixture to cross-link the starch graft copolymer; (3) neutralizing the mixture; (4) precipitating or isolating the cross-linked starch graft copolymer to form particles of SAP product that are sized for use in agricultural applications; and (5) adding the bioactive, growth-promoting additive so that the bioactive, growth-promoting additive is entrapped by the starch matrix. Addition of the bioactive, growth-promoting additive may occur, for example, during at least one of the following processing steps: (1) while graft polymerizing the monomer onto the starch; (2) following neutralization; and (3) following formation of the particles of starch-based SAP product.

Preferred exemplary methods of using the starch-based SAP product including a bioactive, growth-promoting additive to promote plant, seed, seedling, or root growth include (1) placing the starch-based SAP product including a bioactive, growth-promoting additive (or a slurry, mat, or fertilizer including the SAP product) directly onto a growing substrate in proximity to a plant, seed, seedling, or root and (2) applying to a plant, seed, seedling, or root the starch-based SAP product (or a slurry, or fertilizer including the SAP product) and then planting the plant, root, seed, or seedling in the growing substrate. Application of the starch-based SAP product including a bioactive, growth-promoting additive directly to the soil or to a plant, seed, seedling, or root may result in earlier seed germination and/or blooming, decreased irrigation requirements, increased propagation, increased crop growth, increased crop production, and decreased soil crusting. Thus the SAP products made by the above-described methods offer various advantages over prior art SAP products and methods of forming and using SAP products in large-scale agriculture.

Exemplary bioactive, growth-promoting additives include fertilizers, pesticides, bioactive materials, plant-growth hormones, and soil-based nutrients. A list of exemplary pesticides includes acaricides, algicides, antifeedants, avicides, bactericides, bird repellents, chemosterilants, fungicides, herbicide safeners, herbicides, insect attractants, insect repellents, insecticides, mammal repellents, mating disruptors, molluscicides, nematicides, plant activators, plant-growth regulators, rodenticides, synergists, and virucides.

Additional aspects and advantages of this invention will be apparent from the following detailed description of preferred embodiments.

DETAILED DESCRIPTION OF PREFERRED EMBODIMENTS

The present invention generally relates to methods of and products formed by entrapping a bioactive, growth-promoting additive in a starch matrix to form a starch-based SAP product for use in agricultural applications. When applied to a growing substrate in proximity to a plant, root, seed, or seedling, or directly to a plant, root, seed, or seedling, the starch-based SAP product including a bioactive, growth-promoting additive promotes growth of a plant, root, seed, or seedling placed in proximity to the SAP product by promoting the availability of beneficial nutrients to the plant, root, seed, or seedling. The high absorptivity of the starch matrix of the starch-based SAP product facilitates entrapment of the bioactive, growth-promoting additive in the starch matrix, thereby minimizing or eliminating disassociation or release of the bioactive, growth-promoting additive from the starch matrix due to heavy rainfall, squeezing, or jarring of the SAP product during transport or manufacture, and during application of the SAP product. Because the bioactive, growth-promoting additive is entrapped in the SAP product, the runoff rate of the growth-promoting additive is significantly less than the runoff rate of growth-promoting additives applied directly to soil, plants, roots, seedlings, or seeds.

The terms "entrapped" and "encapsulated" as used herein are meant to refer to the fact that the bioactive, growth-promoting additive is physically held by the starch matrix portion of the SAP product. The term "bioactive, growth-promoting additive" is meant to include any additive that promotes plant, root, seedling, or seed growth. Indications of promotion of growth include, but are not limited to, earlier seed germination and/or blooming, decreased irrigation requirements, increased propagation, increased crop growth, increased crop production, increased plant size, increased crop yield, and decreased soil crusting A preferred method of forming an SAP product including a bioactive, growth-promoting additive for use in agricultural applications involves (1) graft polymerizing at least one grafting reagent and a starch to form a starch graft copolymer including a starch matrix; (2) isolating the resulting starch graft copolymer; (3) forming particles of starch graft copolymer that are sized for use in agricultural applications; and (4) adding the bioactive, growth-promoting additive so that at least some of the bioactive, growth-promoting additive is entrapped by the starch matrix. Addition of the bioactive, growth-promoting additive may occur at various times during this process, depending on the type of additive and the desired degree of entrapment of the additive within the starch matrix.

There are at least two preferred implementations of this preferred method of making a starch-based SAP product including a bioactive, growth-promoting additive for use in agricultural applications. A first preferred implementation involves (1) combining a monomer and a starch in the presence of an initiator such that the monomer graft polymerizes onto the starch to form a mixture including a starch graft copolymer having a starch matrix; (2) saponifying the mixture; (3) precipitating the saponified starch graft copolymer from the mixture to form particles of SAP product that are sized for use in agricultural applications; and (4) adding the bioactive, growth-promoting additive so that it is entrapped in the starch matrix. Addition of the bioactive, growth-promoting additive may occur, for example, during at least one of the following processing steps: (1) while combining the monomer and the starch; (2) following saponification of the mixture; and (3) following formation of particles of starch-based SAP product.

With respect to this first preferred implementation, an exemplary preferred monomer is acrylonitrile. The acrylonitrile may be used alone or in conjunction with other monomers, such as, for example, 2-acrylonitrile-2-methyl-propanesulfonic acid, acrylic acid, and acrylamide. These monomers may also be used instead of the polyacrylonitrile. A preferred molar ratio of starch to acrylonitrile is between about 1:1 and about 1:6, and the amount of acrylonitrile in the SAP product is typically proportional to absorbency of the SAP product.

The acrylonitrile is preferably graft polymerized onto the starch in the presence of an initiator, such as a cerium salt. Exemplary preferred cerium salts include, but are not limited to, ceric ammonium nitrate, ammonium persulfate, sodium persulfate, potassium persulfate, ferrous peroxide, ferous ammonium sulfate-hydrogen peroxide, L-ascorbic acid, potassium permanganate-ascorbic acid, derivatives thereof, and mixtures thereof. The graft polymerization process is typically complete within several minutes, producing long, grafted chains of polyacrylonitrile, or polyacrylonitrile in conjunction with other monomers, attached to the starch.

The long, grafted chains of polyacrylonitrile, or polyacrylonitrile in conjunction with other monomers, attached to the starch are then saponified, preferably with potassium hydroxide or sodium hydroxide, to change the nitrile groups into a mixture of carboxamides and alkali carboxylates. Saponification produces a highly viscous mass of saponificate having a dough-like consistency.

The saponificate (either with or without the bioactive, growth-promoting additive) is then precipitated into solid form using a water-miscible solvent such as an alcohol, e.g., methanol, ethanol, propanol, or isopropanol. Since methanol is generally the least expensive alcohol, it is typically preferred. The saponificate is immersed in alcohol, causing the alkali starch graft copolymer to precipitate, forming particles that may be dried and screened to the desired size. The alcohol removes water from, desalts, and granularizes the neutralized starch graft copolymer saponificate. Various precipitation methods using an alcohol exist and could be used in connection with the present invention. Exemplary preferred precipitation methods are discussed in greater detail below.

A second preferred implementation involves (1) combining a monomer and a starch in the presence of an initiator such that the monomer graft polymerizes onto the starch to form a mixture including a starch graft copolymer having a starch matrix; (2) adding a cross-linking agent to the mixture to form a cross-linked starch graft copolymer; (3) neutralizing the mixture; (4) forming particles of SAP product that are sized for use in agricultural applications; and (5) adding the bioactive, growth-promoting additive so that at least some of it is entrapped in the starch matrix. Addition of the bioactive, growth-promoting additive may occur, for example, during at least one of the following processing steps: (1) while graft polymerizing the monomer onto the starch; (2) following neutralization; and (3) following formation of the particles of starch-based SAP product.

With respect to this second preferred implementation, exemplary preferred monomers include, but are not limited to, acrylic acid, acrylamide, methacrylamide, 2-acrylonitrile-2-methyl-propanesulfonic acid, methacrylic acid, vinyl sulfonic acid, ethyl acrylate, derivatives thereof, and mixtures thereof.

The monomer is preferably graft polymerized onto the starch in the presence of an initiator. Exemplary initiators for use in the above-described method include cerium (+4) salts, such as ceric ammonium nitrate; ammonium persulfate; sodium persulfate; potassium persulfate; ferrous peroxide; ferrous ammonium sulfate-hydrogen peroxide; L-ascorbic acid; and potassium permanganate-ascorbic acid. Other suitable initiators known to those skilled in the art may be used. The amount of initiator used will vary based on the chosen initiator, the chosen monomer, and the chosen starch. Some initiators, e.g., persulfates, require the presence of heat. The initiator may be added in a single or multiple steps, and multiple initiators may be used.

Next, a cross-linking agent is added to the mixture to form a cross-linked starch graft copolymer. A cross-linking agent is needed because unless the starch graft copolymer is cross-linked, it may dissolve in aqueous fluid. Cross-linking permits the starch graft copolymer to absorb aqueous fluid without dissolving. The amount of cross-linking agent added is indirectly proportional to the absorbency of the resulting SAP product. Exemplary preferred cross-linking agents include glycerides; diepoxides; diglycidyls; cyclohexadiamide; methylene bis-acrylamide; bishydroxyalkylamides, such as bis hydroxypropyl adipamide; formaldehydes, such as urea-formaldehyde and melamine-formaldehyde resins; isocyanates including di- and tri-isocyanates; epoxy resins, typically in the presence of a base catalyst; derivatives thereof, and mixtures thereof.

Although the use of a cross-linking agent is preferred, self-cross-linking copolymers may also be used. If a self-cross-linking copolymer is used, either a single or multiple self-reactive functional group(s) or multiple co-reactive functional groups are incorporated into the mixture. One exemplary co-reactive functional group is glycidyl methacrylate.

Once a cross-linked starch graft copolymer is formed, the cross-linked starch graft copolymer is neutralized to convert the carboxyl groups to potassium salts, where, for example, potassium hydroxide or potassium methoxide is used to neutralize the starch graft copolymer. In contrast to prior art methods, which require saponification, the neutralization step of the present invention is significantly faster, easier, and less expensive. Also, neutralization does not produce corrosive and dangerous reaction by-products such as ammonia. Exemplary solvents that may be used to effect neutralization include potassium hydroxide, potassium methoxide, and a mixture thereof, any of which may be diluted in methanol.

The resulting neutralized, cross-linked starch graft copolymer is then isolated or precipitated to form particles of SAP product. Exemplary preferred isolation and precipitation methods are discussed in greater detail below. Isolation may occur by any method known to those of ordinary skill in the art, including (1) extrusion and drying, for example, on a double drum dryer, (2) drying the neutralized dough on a double drum dryer to form flakes of the SAP product and later forming particles of the desired size from the flakes of SAP product, (3) tray drying the neutralized dough to form flakes of the SAP product and later forming particles of the desired size from the flakes of SAP product, and (4) forming particles from the neutralized dough and then tray drying these particles.

With respect to both the first and second preferred implementations, the bioactive, growth-promoting additive is preferably added to the SAP dough or particles such that it is substantially distributed throughout. One exemplary preferred method by which addition of the bioactive, growth-promoting additive may occur involves dissolving the additive in a solvent and then spraying the solution of growth-promoting additive onto the SAP dough or onto the particles of SAP product (with or without agitation of the dough or particles during addition). A second preferred method of adding the bioactive, growth-promoting additive involves forming a slurry of additive and adding the slurry to the SAP dough or particles at any point during processing. One advantage of adding the bioactive, growth-promoting additive following formation of the particles of SAP product is that the highly absorptive nature of the particles results in their readily imbibing the additive. In one preferred embodiment, the particles of starch-based SAP product are dried following application of the additive.

Bioactive, growth-promoting additives generally fall into one of two categories: water-soluble additives and water-insoluble additives. Water-soluble additives can be added directly to the SAP dough or particles at any point during processing or during application of the SAP product to the growing substrate. When using the first preferred implementation of the preferred method, the water-soluble additives are preferably added to the SAP dough following saponification or following formation of the particles of SAP product, because addition of the bioactive, growth-promoting additive during combination of the grafting reagent(s) and the starch may result in the additive being washed out during saponification.

Water-insoluble, bioactive, growth-promoting additives can be added at any point during processing, to the SAP particles, or during application of the SAP product to the growing substrate. Typically, water-insoluble additives are dissolved in a solvent, e.g., a water-miscible solvent such as alcohol, and then the solution is applied to the SAP dough, SAP particles, or to the growing substrate. Following application of the solution or slurry of dissolved bioactive, growth-promoting additive, the solvent may be removed from the SAP dough or particles by heating or drying to drive off residual solvent by evaporation.

A preferred proportion of bioactive, growth-promoting additive per pound of SAP product is about 1 oz. per lb. Exemplary bioactive, growth-promoting additives include fertilizers, plant-growth regulators, pesticides, plant-growth hormones, and soil-based nutrients, all of which may be in solid, crystalline, aqueous, or fluid form.

A list of exemplary pesticides includes acaricides, algicides, antifeedants, avicides, bactericides, bird repellents, chemosterilants, fungicides, herbicide safeners, herbicides, insect attractants, insect repellents, insecticides, mammal repellents, mating disruptors, molluscicides, nematicides, plant activators, plant-growth regulators, rodenticides, synergists, virucides, derivatives thereof, blends thereof, and combinations thereof. Three exemplary commercially available pesticides are as follows: Asset™, manufactured by Helena Chemicals of Fairfax, S.C.; ACA™, manufactured by UAP of Greeley, Colo.; and Miracle-Gro™, manufactured by the Scotts Company of Marysville, Ohio.

Exemplary plant-growth regulators include antiauxins, such as, for example, 2,3,5-tri-iodobenzoic acid; auxins, such as, for example, 2,4-D; cytokinins, such as, for example, kinetin; defoliants, such as, for example, metoxuron; ethylene inhibitors; ethylene releasers, such as, for example, ACC and gloxime; gibberellins; growth inhibitors; growth retardants; growth stimulants; derivatives thereof; and mixtures thereof.

A list of exemplary preferred herbicides is as follows: amide herbicides including chloroacetanilide herbicides (such as alachlor and metolachlor); antibiotic herbicides; aromatic acid herbicides including benzoic acid herbicides (such as chloramben and dicamba), phthalic acid herbicides, picolinic acid herbicides, and quinolinecarboxylic acid herbicides; arsenical herbicides; benzoylcyclohexanedione herbicides; benzofuranyl alkylsulfonate herbicides; carbamate herbicides; carbanilate herbicides; cyclohexene oxime herbicides; cyclopropylisoxazole herbicides; dicarboximide herbicides; dinitroaniline herbicides (such as trifluralin and pendimethalin); dinitrophenol herbicides; diphenyl ether herbicides; dithiocarbamate herbicides; halogenated aliphatic herbicides; imidazolinone herbicides; inorganic herbicides; nitrile herbicides; organophosphorus herbicides; phenoxy herbicides (such as 2-4D (also called 2,4-dichlorophenoxy acetic acid) and Mecoprop); phenylenediamine herbicides; pyrazolyloxyacetophenone herbicides; pyrazolylphenyl herbicides; pyridazine herbicides; pyridazinone herbicides (such as Norflurazon™); pyridine herbicides; pyrimidinediamine herbicides; quaternary ammonium herbicides; thiocarbamate herbicides (including butylate and EPTC); thiocarbonate herbicides; thiourea herbicides; triazine herbicides (such as atrazine and simazine); triazinone herbicides (such as Metribuzin™); triazole herbicides; triazolone herbicides; triazolopyrimidine herbicides; uracil herbicides; urea herbicides; Roundup™ (manufactured by Monsanto Co. of St. Louis, Mo.); Chloropropham™; Surflan™ (manufactured by Southern Agricultural Insecticides, Inc. of Palmetto, Fla.); and Clomazone™. A combination or blend of these herbicides may be used.

Exemplary microbial pesticides include bacillus thuringiensis and mycorrhizal fungi. Exemplary insecticides include thiodan, diazinon, and malathion. Exemplary fungicides include Aliette™ (active ingredient=aluminum tris (o-ethylphosphenate)) manufactured by Bayer Crop Science of Research Triangle Park, N.C.; Rovral™ (active ingredient=iprodione) manufactured by Bayer Crop Science of Research Triangle Park, N.C.; Mancozeb™; Sovran™ (active ingredient=kresoxim-methyl) manufactured by BASF Agolutions of Canada; Flint™ (active ingredient=trifloxystrobin) manufactured by Novartis Corporation; Ridomil™ (active ingredient=Mefenoxam) and Ridomil Gold™ (active ingredient methoxyacetylamino-®-2-2[2,6-dimethylphenyl-propionic acid methyl ester] manufactured by Syngenta Crop Protection Inc. of Greensboro, N.C.; Dividend™ (active ingredient=difenoconazole) manufactured by Syngenta Crop Protection Inc. of Greensboro, N.C.; SoilGard™ (active ingredient=gliocladium virens) manufactured by Certis USA of Columbia, Md.; Bravo™ (active ingredient=chlorothalonil) manufactured by Syngenta Crop Protection Inc. of Greensboro, N.C.; Vitavax™ (active ingredient=carboxin) manufactured by Gustafson LLC of Canada; Thiram™ (active ingredient=tetramethylthiuram disulfide) manufactured by Gustafson LLC of Canada; Maxim™ (active ingredient=fludioxonil) manufactured by Syngenta Crop Protection Inc. of Greensboro, N.C.; Quadris™ (active ingredient=azoxystrobin) manufactured by Syngenta Crop Protection Inc. of Greensboro, N.C.; and Elite™ (active ingredient=tebuconazole) manufactured by Bayer Crop Science of Research Triangle Park, N.C. A combination or blend of these may be used.

A list of exemplary soil-based nutrients includes calcium, magnesium, potassium, phosphorus, boron, zinc, manganese, copper, iron, sulfur, nitrogen, molybdenum, ammonium phosphate, fish meal, derivatives thereof, blends thereof, and mixtures thereof. More information about exemplary growth-promoting additives can be found in The Farm Chemicals Handbook published by Meister Publishing Company, 1992.

Exemplary starches for use in connection with the above-identified methods include pure starches, flours, and meals. Preferred starches include cornstarch, corn meal, wheat starch, sorghum starch, tapioca starch, cereal flours and meals, banana flour, yucca flour, peeled yucca root, unpeeled yucca root, oat flour, banana flour, and tapioca flour. Combinations, derivatives, and blends of these starches may also be used. These starch sources are preferably gelatinized to optimize absorbency. Exemplary commercially available starches include native starches (e.g., corn starch (e.g., Pure Food Powder™, manufactured by A.E. Staley), waxy maize starch (e.g., Waxy™ 7350, manufactured by A.E. Staley), wheat starch (e.g., Midsol™ 50, manufactured by Midwest Grain Products), and potato starch (e.g., Avebe™, manufactured by A.E. Staley)), dextrin starches (e.g., Stadex™ 9, manufactured by A.E. Staley), dextran starches (e.g., Grade 2P, manufactured by Pharmachem Corp.), corn meal, peeled yucca root, unpeeled yucca root, oat flour, banana flour, tapioca flour, and industrial-grade unmodified cornstarch. A preferred molar ratio of the starch to the monomer is between about 1:1 and about 1:6.

As mentioned above, various preferred isolation methods can be used in connection with the present invention. Isolation can occur by precipitation or by drying and/or manipulation of the SAP dough. Precipitation can be used to form particles, granules, powders, strands, rods, films, and the like, all of which are referred to herein as "particles." Some preferred precipitation methods involve adding a water-miscible solvent such as, for example, an alcohol, e.g., methanol, ethanol, propanol, or isopropanol. One preferred method of alcohol-based precipitation involves immersing the starch graft copolymer in alcohol, thereby causing the starch graft copolymer to precipitate into particles that are later screened to the desired size after drying. The alcohol removes the water from, removes extraneous salts from, and granularizes the starch graft copolymer.

A second preferred method of alcohol-based precipitation involves blending sufficient alcohol into the starch graft copolymer to achieve a smooth dispersion. The smooth dispersion is then pumped into a precipitation tank including a stirring system that can vigorously mix the alcohol while the smooth starch graft copolymer dispersion is added. Once mixed, the resulting alcohol and starch graft copolymer particles are either (1) collected by decanting or washing with alcohol or (2) centrifuged and collected, then dried to a moisture level of between about 1 percent and about 20 percent.

A third preferred method of alcohol-based precipitation involves wetting the surface of the saponificate or neutralized starch graft copolymer with a small amount of alcohol and then chopping the starch graft copolymer into larger "chunks" that will not re-adhere to one another. Once the surface of the saponificate or neutralized starch graft copolymer has been wetted with alcohol, the resulting material is slippery to the touch and is no longer sticky. This effect may be achieved, for example, by using a compositional ratio of between about one part and about two parts of methanol per one part of solid. Once the alcohol has been added, the saponificate or neutralized starch graft copolymer is either (1) pumped through an in-line chopper to form chunks having a diameter of less than one inch or (2) hand-chopped with scissors. The resulting mixture is then fed into a tank or Waring blender that has between about 1.5 gallons and about 2.0 gallons of additional alcohol per pound of starch graft copolymer. The alcohol in the larger tank is agitated with a Cowles dissolver or other mixer capable of achieving high speeds.

A fourth preferred method of alcohol-based precipitation involves pre-forming the particle size before the alcohol-based precipitation. The use of dies to form strands or rods having different shapes and diameters can greatly improve the particle-size formation process. This fourth method offers enhanced control of the final particle size. The starch graft copolymer (neutralized or unneutralized) is forced through a die plate having holes of varying diameter (e.g., about 1/16 inch to more than 1/4 inch) and varying shape (e.g., round, star, ribbon, etc.). Methods of forcing the starch graft copolymer through the die plate include using a hand-operated plunger, screw-feeding, auguring, pumping, and any other commonly known method. The resulting strands or rods are placed into the precipitation tank without any further addition of alcohol as a premixing agent. The strands or rods may be treated to prevent them from sticking together, by, for example, wetting the strands or rods with alcohol or dusting them with a dusting agent, such as, for example, cellulose, clay, starch, flour, or other natural or synthetic polymers. Alternatively, the strands or rods may be lightly sprayed with alcohol to prevent them from sticking together. The resulting strands or rods are precipitated with agitated alcohol, removed from the tank, and dried.

A exemplary method of isolating the starch graft copolymer that does not involve adding alcohol involves drying the starch graft copolymer on a heated drum or via air-drying. The resulting particles of SAP produce are then manipulated to form a final SAP product having a size and form appropriate for the desired agricultural application. Because the second preferred implementation of the method of forming an SAP product including a bioactive, growth-promoting additive forms a neutralized, cross-linked starch graft copolymer that is a relatively pure system containing very little extraneous salt, isolation of the SAP product formed using this implementation can be effected by merely drying the SAP product. In contrast, prior art starch graft copolymers contain a significant amount of extraneous salt and ammonia and thus must be treated with an alcohol, typically methanol. The use of methanol significantly adds to the cost of producing the SAP product because methanol disposal is very expensive.

Another exemplary method of isolating the starch graft copolymer without adding alcohol involves extruding the neutralized, cross-linked starch graft copolymer through a heated screw to form particles of SAP product. To minimize re-agglomeration of the particles, the particles are preferably coated with a dusting agent that decreases their propensity to stick together. Exemplary dusting agents include cellulose, clay, starch, flour, and other natural or synthetic polymers that prevent the particles from sticking together. Alternatively, the particles may be lightly sprayed with methanol to prevent them from sticking together, and/or the extrusion can be performed under high pressure.

Where the SAP product is used in particle form, the preferred particle size of the starch-based SAP product depends on the specific agricultural application intended. A preferred particle size for agricultural applications that deposit the starch-based SAP product directly onto the growing substrate is less than 50 mesh, more particularly between about 8 mesh and about 25 mesh. This particle size is preferred because commercially available granular applicators require this particle size. To broadcast or meter the starch-based SAP particles through existing agricultural application equipment, an 8-mesh to about 25-mesh granular, starch-based SAP product having a density of between about 25 lbs per cubic foot and about 35 lbs per cubic foot, with 32 lbs per cubic foot most preferred.

Other agricultural applications, such as seed coating and root dipping, use a finer particle size. For seed coating, the desired particle size is between about 75 mesh and about 200 mesh, more preferably about 100 mesh. For root coating, the desired particle size is between about 30 mesh and about 100 mesh, more preferably about 50 mesh. Further, the release rate of the starch-based SAP product is affected by its particle size. For example, preliminary results suggest that pelletized particles may release the active portion of the bioactive, growth-promoting additive more gradually than granular products of equal surface area.

Fillers, absorbents, carriers, and surfactants whose presence affects the processability or efficacy of the bioactive, growth-promoting additive may be used to form the starch-based SAP product. Exemplary carriers include Kaolin clay, Fullers Earth, diatomaceous earth products, ungelatinized granular starch, silicates, blends thereof, mixtures thereof, and derivatives thereof. Typically, the swellability of the starch-based SAP product decreases with increased proportions of clay. The processing point at which the fillers, absorbents, carrier, and surfactants are added may vary depending upon the desired characteristics of the resulting SAP product. Two exemplary preferred points of addition of a filler, absorbent, carrier, or surfactant are (1) preblending with the starch and (2) separate addition during downstream processing.

SAP products including a bioactive, growth-promoting additive may be used in connection with any crop. A list of exemplary crops is as follows: alfalfa, asparagus, barley, beans (including lima beans, snap beans, and green beans), broccoli, canola, carrots, cauliflower, celery, coriander, coreopsis, cotton, cucumbers, dill, elymus glaucus, field corn (including sweet corn), fine fescue, garlic, kentucky bluegrass, lentils, lettuce (including mesclin, head lettuce, leaf lettuce, romaine lettuce, and cabbage), oats, onions, melons (including watermelon, cantaloupe, and honeydew), mushrooms, parsley, peas (dry), peppers (including bell peppers), potatoes, pumpkins, radishes, rye grass, sod, sorghum, soybeans, spinach, squash, sugar beets, sunflowers, Swiss chard, tall fescue, tobacco, tomatoes, turnips, wheat, white clover, wild rye, and zinnia.

Application of the SAP product to a plant, root, seed, or seedling may occur by any method known to one of ordinary skill, including, but not limited to, dipping the plant, root, seed, or seedling into SAP product particles, a slurry of SAP product particles, or a paste including the SAP product particles; mixing dirt, soil, fertilizer, or another growing substrate with the SAP product particles and later planting a plant, root, seed, or seedling into the growing substrate/SAP product mixture; and forming a slurry of SAP product that is applied directly to the growing substrate.

Preferred exemplary methods of using the starch-based SAP product including a bioactive, growth-promoting additive to promote plant, seed, seedling, or root growth include (1) placing the starch-based SAP product including a bioactive, growth-promoting additive (or a slurry, mat, or fertilizer including the SAP product) directly onto a growing substrate in proximity to a plant, seed, seedling, or root and (2) applying to a plant, seed, seedling, or root the starch-based SAP product (or a slurry or fertilizer including the SAP product) and then planting the plant, root, seed, or seedling in the growing substrate. One exemplary method of preparing a slurry for use as a root dip involves combining between about 3 oz. and about 6 oz. of SAP product with about 5 gallons of water to form a slurry that is applied to the growing substrate and/or to the plant, root, seed, or seedling. One exemplary method of preparing a seed coating including the SAP product involves combining a binding agent and the SAP product with a solvent, preferably water, to form a slurry that is applied to the seed. Alternatively, the dry SAP product may be combined with a binder or tackifier, such as, for example, a mineral, gypsum, or clay, to form a mixture that will stick to the seed. These methods can also be used to prepare a coating to be applied to any of a plant, root, seed, or seedling.

The inventors of the present invention recognize that entrapment efficiency, swellability, release rate, and efficacy of the starch-based SAP product can be affected to various degrees by the types of materials used, the processing conditions implemented, and the degree and type of ex-situ downstream processing. Because composition and processing conditions are selected to maximize product performance and processing efficiency, preferred processing parameters, such as, for example, temperature, solids concentration, concentration of starch, concentration of growth-promoting additive, type of additive, number of additives, levels of addition, addition processes, and addition timing, vary greatly. For this reason, the following examples are intended only to further illustrate the invention and are not intended to limit the scope of the invention.

EXAMPLE 1

Spray Application of Asset™ Pesticide to SAP Particles

Distilled water (1,400 ml) was placed in a 3-liter resin kettle and was subjected to constant agitation with a stirrer. Starch flour or meal (110 g) was slowly added to the kettle, and the resulting mixture was stirred for approximately five minutes. A slow stream of nitrogen gas was added to the mixture while the mixture was heated until it reached a temperature of approximately 95° C. Upon reaching this temperature, the mixture was maintained at this temperature and stirred for approximately 45 minutes to ensure that the starch was gelatinized. The heating mantle was then removed, and the resin kettle was placed in a cold-water bucket bath. The mixture was continuously stirred under nitrogen until the temperature reached 25° C. Acrylonitrile (115 g) and 2-acrylamido-2-methyl-propanesulfonic acid (23 g) were added. The resulting mixture was continuously stirred under nitrogen for approximately 10 minutes. A catalyst solution including cerium ammonium nitrate (5.5 g) dissolved in 0.1 M nitric acid solution (50 ml) was added to the mixture while the mixture cooled. The mixture was continuously stirred under nitrogen while the resin kettle remained in the cold-water bucket for approximately 60 minutes. The temperature of the mixture at the end of the 60 minutes was approximately 40° C. A solution including potassium hydroxide flakes (90 g) dissolved in water (200 g) was added to the mixture during stirring and heating. The mixture was stirred and heated until a temperature of 95° C. was achieved, after which the mixture was stirred for an additional 60 minutes. The mixture was then neutralized to a pH of 7.5 using a 10% solution of hydrochloric acid. The resulting dough was then cooled to a temperature of about 40° C. The viscous dough was precipitated in methanol using one of the above-described precipitation methods to produce SAP particles.

The resulting SAP particles were subjected to a Fertilizer Analysis Test that analyzed the presence of various bioactive components. The results are reproduced in Table I to allow the reader to compare the SAP product with the starch-based SAP product of the present invention.

TABLE I

Fertilizer Analysis of an SAP Product Without an Additive.

| Nutrient | % Available |
|---|---|
| Nitrogen | 3.04 |
| Ammonia | <0.01 |
| Phosphorus | <0.10 |
| $P_2O_5$ | N/A |
| Potassium | 17.66 |
| $K_2O$ | 21.28 |
| Calcium | <0.01 |
| Magnesium | <0.01 |
| Sodium | 0.08 |
| Boron | <20.0 |
| Iron | 39.96 |
| Manganese | <10.0 |
| Copper | <10.0 |
| Zinc | <10.0 |
| Monoammonium Phosphate | N/A |

Trial A: Application of Asset™ Pesticide at a Concentration of 3 Pints/Acre

Using a standard, commercially available garden sprayer, approximately 3 pints of Asset™ was sprayed onto 10 lbs. of SAP product having a mesh size of between about 10 and about 20 and formed using the above-described method. The SAP particles were agitated during application of the Asset™ pesticide, to ensure that the bioactive, growth-promoting additive thoroughly coated the SAP particles. Asset™ pesticide has a slight green tint, and thus the application of Asset™ pesticide to the SAP particles resulted in their being slightly tinted green. The resulting starch-based SAP particles were subjected to a Fertilizer Analysis Test that analyzed the presence of various bioactive components. The results are reproduced in Table II.

TABLE II

| Fertilizer Analysis of the SAP Product Formed in Trial A. | |
|---|---|
| Nutrient | % Available |
| Nitrogen | 3.85 |
| Ammonia | 0.13 |
| Phosphorus | 2.61 |
| $P_2O_5$ | 5.97 |
| Potassium | 16.06 |
| $K_2O$ | 19.35 |
| Calcium | <0.01 |
| Magnesium | <0.01 |
| Sodium | 0.13 |
| Boron | 74.08 |
| Iron | 288.93 |
| Manganese | 165.65 |
| Copper | 151.97 |
| Zinc | 160.67 |
| Monoammonium Phosphate | 1.07 |

Trial B: Application of Asset™ Pesticide at a Concentration of 8 Pints/Acre

Using a standard, commercially available garden sprayer, approximately 8 pints of Asset™ pesticide was sprayed onto 10 lbs of SAP product having a mesh size of between about 10 and about 20 and formed using the above-described method. The SAP particles were agitated during application of the Asset™ pesticide, to ensure that the bioactive, growth-promoting additive thoroughly coated the SAP particles. Asset™ pesticide has a slightly green tint, and thus the application of Asset™ pesticide to the SAP particles resulted in their being slightly tinted green. The resulting starch-based SAP particles were subjected to a Fertilizer Analysis Test that analyzed the presence of various bioactive components. The results are reproduced in Table III.

TABLE III

| Fertilizer Analysis of the SAP Product Formed in Trial B. | |
|---|---|
| Nutrient | % Available |
| Nitrogen | 4.76 |
| Ammonia | 0.62 |
| Phosphorus | 5.90 |
| $P_2O_5$ | 13.51 |
| Potassium | 15.07 |
| $K_2O$ | 18.16 |
| Calcium | <0.01 |
| Magnesium | <0.01 |
| Sodium | 0.20 |
| Boron | 166.17 |
| Iron | 629.38 |
| Manganese | 373.84 |
| Copper | 340.36 |
| Zinc | 353.38 |
| Monoammonium Phosphate | 5.09 |

EXAMPLE 2

Slurry Application of Asset™ Pesticide to SAP Particles

SAP particles having a mesh size of between about 20 and about 40 were made according to the method described in Example 1. Approximately 25 g of SAP particles were combined with 1 L of an aqueous slurry of Asset™ pesticide. The resulting slightly green-tinted slurry was agitated to ensure that the Asset™ pesticide was evenly distributed throughout the slurry. The slurry was subjected to a Fertilizer Analysis Test that analyzed the presence of various bioactive components. The results are reproduced in Table IV.

TABLE IV

| Fertilizer Analysis of the SAP Product of Example 2. | |
|---|---|
| Nutrient | % Available |
| Nitrogen | 5.66 |
| Ammonia | 2.47 |
| Phosphorus | 7.96 |
| $P_2O_5$ | 18.24 |
| Potassium | 3.94 |
| $K_2O$ | 4.74 |
| Calcium | <0.01 |
| Magnesium | <0.01 |
| Sodium | 0.18 |
| Boron | 219.79 |
| Iron | 847.58 |
| Manganese | 673.47 |
| Copper | 452.49 |
| Zinc | 462.74 |
| Monoammonium Phosphate | 20.28 |

EXAMPLE 3

Spray Application of Miracle-Gro™ Pesticide to SAP Particles

SAP particles having a mesh size of between about 10 and about 20 were made according to the method described in Example 1. Between about 6 pints and about 8 pints of Miracle-Gro™ pesticide was sprayed onto about 1 lb. of SAP product using a standard, commercially available garden sprayer. The resulting particles of starch-based SAP product were agitated to ensure that the Miracle-Gro™ pesticide was evenly distributed. Following spraying, the SAP particles were slightly tinted green.

EXAMPLE 4

Inclusion of Miracle-Gro™ Pesticide in the SAP Dough

Distilled water (1,400 ml) was placed in a 3-liter resin kettle and was subjected to constant agitation with a stirrer. Starch flour or meal (110 g) was slowly added to the kettle, and the resulting mixture was stirred for approximately five minutes. A slow stream of nitrogen gas was added to the mixture while the mixture was heated until it reached a temperature of approximately 95° C. The mixture was maintained at this temperature and stirred for approximately 45 minutes to ensure that the starch was gelatinized. The heating mantle was then removed, and the resin kettle was placed in a cold-water bath. The mixture was continuously stirred under nitrogen until the temperature reached 25° C. Acrylonitrile (115 g) and 2-acrylamido-2-methyl-propanesulfonic acid (23 g) were added. The resulting mixture was continuously stirred under nitrogen for approximately 10 minutes. A catalyst solution including cerium ammonium nitrate (5.5 g) dissolved in 0.1M nitric acid solution (50 ml) was added to the mixture while the mixture cooled. The mixture was continuously stirred under nitrogen while the resin kettle remained in the cold-water bath for approximately 60 minutes. The temperature of the mixture at the end of the 60 minutes was approximately 40° C. A solution including potassium hydroxide flakes (90 g) dissolved in water (200 g) was added to the mixture during stirring and heating. The mixture was stirred and heated until a temperature of 95° C. was achieved, after which the mixture was stirred for an additional 60 minutes. The mixture was then neutralized to a pH of 7.5 using a 10% solution of hydrochloric acid. The dough was then cooled to a temperature of about 40° C. Approximately 12 pints of liquid Miracle-Gro™ pesticide was added to about one lb. of dough. The resulting slightly green-tinted dough was agitated for approximately 30 minutes to ensure intimate mixing of the Miracle-Gro™ pesticide and the SAP dough. The resulting dough was extruded into granules. In one implementation, a pasta maker was used to extrude rod-shaped granules. Following extrusion, the granules were dried. Because the rod-shaped granules were sticky, they were dusted with sufficient clay, starch, flour, cellulose, or celite to remove the stickiness. In one implementation, the rod-shaped granules were ground into particles having a desired particle size. Optionally, fine particles could be formed into pellets having a desired size. The process of pelletizing is well known to those skilled in the art.

EXAMPLE 5

Inclusion of Ammonium Phosphate in the SAP Dough

Distilled water (1,400 ml) was placed in a 3-liter resin kettle and was subjected to constant agitation with a stirrer. Starch flour or meal (115 g) was slowly added to the kettle, and the resulting mixture was stirred for approximately five minutes. A slow stream of nitrogen gas was added to the mixture while the mixture was heated until it reached a temperature of approximately 95° C. The mixture was maintained at this temperature and stirred for approximately 45 minutes to ensure that the starch was gelatinized. The heating mantle was then removed, and the resin kettle was placed in a cold-water bath. The mixture was continuously stirred under nitrogen until the temperature reached 25° C. Acrylonitrile (115 g) and 2-acrylamido-2-methyl-propanesulfonic acid (23 g) were added. The resulting mixture was continuously stirred under nitrogen for approximately 10 minutes. A catalyst solution including cerium ammonium nitrate (5.5 g) dissolved in 0.1M nitric acid solution (50 ml) was added to the mixture while the mixture was cooled. The mixture was continuously stirred under nitrogen while the resin kettle remained in the cold-water bath for approximately 60 minutes. The temperature of the mixture at the end of the 60 minutes was approximately 40° C. A solution including potassium hydroxide flakes (90 g) dissolved in water (200 g) was added to the mixture during stirring and heating. The mixture was stirred and heated until a temperature of 95° C. was achieved, after which the mixture was stirred for an additional 60 minutes. The mixture was then neutralized to a pH of 7.5 using a 10% solution of hydrochloric acid. The dough was then cooled to a temperature of about 40° C. Approximately 36.5 g of ammonium phosphate was added directly to about one lb. of dough. The resulting dough was agitated for approximately 30 minutes to ensure intimate mixing of the ammonium phosphate and the SAP dough. The resulting dough was extruded into granules. In one implementation, a pasta maker was used to extrude rod-shaped granules. Following extrusion, the granules were dried. Because the rod-shaped granules were sticky, they were dusted with sufficient clay, starch, flour, cellulose, or celite to remove the stickiness. In one implementation, the rod-shaped granules were ground into particles having a desired particle size. Optionally, fine particles could be formed into pellets having a desired size. The process of pelletizing is well known to those skilled in the art.

In general, optimal levels of entrapment of bioactive, growth-promoting additive occur when the starch is highly gelatinized by a combination of mechanical and thermal energy, because a highly gelatinized starch will undergo a greater degree of hydrogen bonding than will a partially gelatinized starch, resulting in a more gradual release rate. In contrast, lower processing temperatures can be used to increase the release rate of the granular, starch-based SAP product.

One benefit offered by the starch-based SAP product including a bioactive, growth-promoting additive is that it excels at carrying nutrients to seedling, roots, seeds, and plants. Further, starch controlled-release matrices provide a reduction in leaching, groundwater contamination, toxicity, odor, volatility, and decompositional problems compared to prior art application of fertilizers not entrapped in a starch matrix. The abundant availability, low cost, and physical nature of starches (especially cornstarch) in the United States make the starch-based SAP product including a bioactive, growth-promoting additive relatively inexpensive to manufacture.

Another benefit of the starch-based SAP product including a bioactive, growth-promoting additive is that it provides controlled-release technology designed to extend the period of time over which the active portion of the bioactive, growth-promoting additive is released into a growing environment. Two objectives of controlled release are (1) to improve efficacy and (2) to reduce negative environmental consequences of bioactive, growth-promoting additive application.

One advantage of the second preferred implementation of the method of forming the starch-based SAP product including a bioactive, growth-promoting additive is elimination of the saponification step. Saponification has various drawbacks. First, saponification requires expensive machinery and generates ammonia, which is corrosive, costly to remove, and expensive to dispose of. Second, the potassium hydroxide (KOH) added during saponification makes the saponified starch graft copolymer mixture basic, and acid, e.g., hydrochloric acid, nitric acid, sulfuric acid, or phosphoric acid, must be added to the mixture in order to neutralize the pH of the starch graft copolymer mixture. If the amount of acid that must be added is significant, the absorbency of the SAP is reduced. Third, the saponification waste solutions are expensive to dispose of because they include potassium and ammonium salts and other extraneous salts. Fourth, acrylonitrile is hazardous to use and expensive to dispose of.

In one preferred embodiment, the active portion of the bioactive, growth-promoting additive is withdrawn from the starch matrix by capillary action of the plant, root, or seedling. In an alternative preferred embodiment, seeds utilize the active portion of the bioactive, growth-promoting additive as it slowly diffuses from the starch matrix. One way that diffusion occurs is as follows: particles of the SAP product including a bioactive, growth-promoting additive imbibe water, swell, and thereby allow the active portion of the bioactive, growth-promoting additive entrapped in the starch matrix to slowly diffuse out of the particles. Temperature and microbial activity can affect the rate of release, including the rate of diffusion.

It will be obvious to those having skill in the art that many changes may be made to the details of the above-described embodiments without departing from the underlying principles of the invention. The scope of the present invention should, therefore, be determined only by the following claims.

The invention claimed is:

1. A method of forming a superabsorbent polymer product including a bioactive, growth-promoting additive for use in agricultural applications, comprising:
   combining a grafting reagent and a starch such that the grafting reagent graft polymerizes onto the starch to form a mixture including starch graft copolymers, the starch graft copolymers forming a starch matrix;
   isolating the starch graft copolymers;
   forming particles including the starch graft copolymers, the particles sized between about 8 and 25 mesh, wherein forming particles sized between about 8 and 25 mesh comprises extruding the starch graft copolymers into strands and granularizing the strands to form granular, non-powder starch graft copolymer particles sized between about 8 and 25 mesh isolated through screening;
   applying an alcohol to the strands to reduce tackiness of the extruded strands of the starch graft copolymers, the alcohol chosen from methanol, ethanol, propanol or isopropanol; and
   adding the bioactive, growth-promoting additive while combining the grafting reagent and the starch to form the starch graft copolymers, such that at least some of the bioactive, growth-promoting additive is entrapped by the starch matrix.

2. The method of claim 1, further comprising:
   adding a cross-linking agent to the mixture to form cross-linked starch graft copolymers, the cross-linking starch graft copolymers formed prior to extruding the starch graft copolymers into strands; and
   neutralizing the cross-linked starch graft copolymers.

3. The method of claim 2, in which the cross-linking agent is selected from a group consisting essentially of glycerides, diepoxides, diglycidyls, cyclohexadiamide, methylene bis-acrylamide, bis-hydroxyalkylamides, bis-hydroxypropyl adipamide, formaldehydes, urea-formaldehyde, melamine-formaldehyde resins, isocyanates, di-isocyanates, tri-isocyanates, epoxy resins, self-cross-linking polymers, derivatives thereof, and mixtures thereof.

4. The method of claim 1, further comprising:
   saponifying the mixture.

5. The method of claim 1, in which combining the grafting reagent and the starch involves graft polymerizing a monomer onto the starch in the presence of an initiator.

6. The method of claim 5, in which the monomer is selected from a group consisting essentially of acrylonitrile, acrylic acid, acrylamide, 2-acrylonitrile-2-methyl-propanesulfonic acid, methacrylamide, methacrylic acid, vinyl sulfonic acid, ethyl acrylate, derivatives thereof, and mixtures thereof.

7. The method of claim 5, in which the starch and the monomer are present in a molar ratio of between about 1:1 and about 1:6.

8. The method of claim 5, in which the initiator is a cerium salt.

9. The method of claim 1, in which the starch is selected from a group consisting essentially of pure starches, flours, meals, and mixtures thereof.

10. The method of claim 1, in which the starch is a gelatinized starch.

11. The method of claim 1, in which forming the particles involves precipitating the starch graft copolymers by one of (1) adding to the mixture a sufficient amount of an alcohol to cause the starch graft copolymers to form a precipitate, and (2) mechanically manipulating the mixture such that it forms a precipitate.

12. The method of claim 1, in which forming the particles involves drying the mixture.

13. The method of claim 1, in which a ratio of bioactive, growth-promoting additive to starch is between about 0.5 oz.:1 lb. and about 1.5 oz.:1 lb.

14. The method of claim 1, in which the bioactive, growth-promoting additive is selected from a group consisting essentially of fertilizers, pesticides, bioactive materials, plant-growth hormones, plant-growth regulators, soil-based nutrients, derivatives thereof, and mixtures thereof.

15. The method of claim 1, further comprising:
   adding a material selected from a group consisting essentially of fillers, absorbents, carriers, surfactants, derivatives thereof, and mixtures thereof.

16. The method of claim 1, further comprising:
   applying the superabsorbent polymer product including the bioactive, growth-promoting additive to one of (1) a growing substrate in proximity to one of a plant, seedling, root, and seed and (2) to one of a plant, a seedling, a root, and a seed.

17. A method of forming a superabsorbent polymer product including a bioactive, growth-promoting additive for use in agricultural applications, comprising:
   combining a monomer and a starch in the presence of an initiator such that the monomer graft polymerizes onto the starch to form a mixture including starch graft copolymers, the starch graft copolymers forming a starch matrix;
   saponifying the mixture;
   precipitating the starch graft copolymers from the saponified mixture to form particles of superabsorbent polymer product sized for use in agricultural applications; and adding the bioactive, growth-promoting additive while precipitating the starch graft copolymers, such that at least a portion of the bioactive, growth-promoting additive is entrapped by the starch matrix;

wherein forming particles of superabsorbent polymer product comprises forcing the starch graft copolymer into strands through a die plate having holes disposed therein with a diameter of between about $\frac{1}{16}$ inch to $\frac{1}{4}$ inch, applying an alcohol to the strands to reduce tackiness of the strands of the starch graft copolymers, the alcohol chosen from methanol, ethanol, propanol or isopropanol, the strands subsequently being granularized to form granular, non-powder starch graft copolymer particles sized between about 8 and 25 mesh isolated through screening.

18. The method of claim 17, in which the monomer is selected from a group consisting essentially of acrylonitrile, acrylic acid, acrylamide, 2-acrylonitrile-2-methyl-propane-sulfonic acid, methacrylamide, methacrylic acid, vinyl sulfonic acid, ethyl acrylate, derivatives thereof, and mixtures thereof.

19. The method of claim 17, in which the starch and the monomer are present in a molar ratio of between about 1:1 and about 1:6.

20. The method of claim 17, in which the initiator is a cerium salt.

21. The method of claim 17, in which the starch is selected from a group consisting essentially of pure starches, flours, meals, and mixtures thereof.

22. The method of claim 17, in which precipitating the starch graft copolymers involves at least one of (1) adding a sufficient amount of an alcohol to the saponified mixture to cause it to form a precipitate and (2) mechanically manipulating the saponified mixture such that it forms a precipitate.

23. The method of claim 17, in which the bioactive, growth-promoting additive is selected from a group consisting essentially of fertilizers, pesticides, bioactive materials, plant-growth regulators, plant-growth hormones, soil-based nutrients, derivatives thereof, and mixtures thereof.

24. The method of claim 17, further comprising:
applying the particles of superabsorbent polymer product including the bioactive, growth-promoting additive to one of (1) a growing substrate in proximity to one of a plant, seedling, root, and seed and (2) to one of a plant, a seedling, a root, and a seed.

25. A method of forming a superabsorbent polymer product including a bioactive, growth-promoting additive for use in agricultural applications, comprising:
combining a monomer and a starch in the presence of an initiator such that the monomer graft polymerizes onto the starch to form a mixture including starch graft copolymers, the starch graft copolymers forming a starch matrix;
adding a cross-linking agent to the mixture to form cross-linked starch graft copolymers;
neutralizing the mixture;
forming particles of the superabsorbent polymer product for use in agricultural applications, the particles being sized between about 8 and 25 mesh, wherein forming particles sized between about 8 and 25 mesh comprises extruding the cross-linked starch graft copolymers into strands subsequent to forming cross-linked starch graft copolymers;

applying an alcohol to the strands to reduce tackiness of the extruded strands of the starch graft copolymers, the alcohol chosen from methanol, ethanol, propanol or isopropanol, and granularizing the strands to form granular, non-powder starch graft copolymer particles sized between about 8 and 25 mesh isolated through screening; and adding the bioactive, growth-promoting additive to the starch graft copolymers after forming the superabsorbent polymer particles for use in agricultural applications, such that at least a portion of the bioactive, growth-promoting additive is entrapped by the starch matrix.

26. The method of claim 25, in which the monomer is selected from a group consisting essentially of acrylonitrile, acrylic acid, acrylamide, 2-acrylonitrile-2-methyl-propane-sulfonic acid, methacrylamide, methacrylic acid, vinyl sulfonic acid, ethyl acrylate, derivatives thereof, and mixtures thereof.

27. The method of claim 25, in which the starch and the monomer are present in a molar ratio of between about 1:1 and about 1:6.

28. The method of claim 25, in which the initiator is a cerium salt.

29. The method of claim 25, in which the starch is selected from a group consisting essentially of pure starches, flours, meals, and mixtures thereof.

30. The method of claim 25, in which forming particles of superabsorbent polymer product involves at least one of (1) adding a sufficient amount of an alcohol to the mixture to cause it to form a precipitate and (2) mechanically manipulating the mixture such that it forms a precipitate.

31. The method of claim 25, in which the bioactive, growth-promoting additive is selected from a group consisting essentially of fertilizers, pesticides, bioactive materials, plant-growth hormones, plant-growth regulators, soil-based nutrients, derivatives thereof, and mixtures thereof.

32. The method of claim 25, further comprising:
applying the particles of superabsorbent polymer product including the bioactive, growth-promoting additive to one of (1) a growing substrate in proximity to one of a plant, seedling, root, and seed and (2) to one of a plant, a seedling, a root, and a seed.

33. The method of claim 1, wherein extruding the starch graft copolymers into strands comprises extruding the starch graft copolymers into strands having a diameter of between about $\frac{1}{16}$ inch to $\frac{1}{4}$ inch.

34. The method of claim 25, wherein extruding the neutralized mixture into strands comprises extruding the cross-linked starch graft copolymers into strands having a diameter of between about $\frac{1}{16}$ inch to $\frac{1}{4}$ inch.

* * * * *